US009216228B2

(12) United States Patent
Kratz

(10) Patent No.: US 9,216,228 B2

(45) Date of Patent: Dec. 22, 2015

(54) RECEPTOR AND ANTIGEN TARGETED PRODRUG

(75) Inventor: Felix Kratz, Ehrenkirchen (DE)

(73) Assignee: KTB Tumorforschungsgesellschaft MBM, Freiburg im Breisgau (DE)

( * ) Notice: Subject to any disclaimer, the term of this patent is extended or adjusted under 35 U.S.C. 154(b) by 1173 days.

(21) Appl. No.: 12/525,453

(22) PCT Filed: Feb. 15, 2008

(86) PCT No.: PCT/EP2008/001187

§ 371 (c)(1), (2), (4) Date: Jul. 31, 2009

(87) PCT Pub. No.: WO2008/098788

PCT Pub. Date: Aug. 21, 2008

(65) Prior Publication Data

US 2010/0111866 A1 May 6, 2010

(30) Foreign Application Priority Data

Feb. 16, 2007 (EP) .................................... 07003341

(51) Int. Cl.

| | |
|---|---|
| ***C07K 7/06*** | (2006.01) |
| ***A61K 47/48*** | (2006.01) |
| ***A61K 49/00*** | (2006.01) |
| ***A61K 51/06*** | (2006.01) |
| ***B82Y 5/00*** | (2011.01) |

(52) U.S. Cl.

CPC ....... *A61K 47/48238* (2013.01); *A61K 47/4813* (2013.01); *A61K 47/48046* (2013.01); *A61K 47/48092* (2013.01); *A61K 47/48107* (2013.01); *A61K 47/48246* (2013.01); *A61K 47/48284* (2013.01); *A61K 47/48338* (2013.01); *A61K 47/48346* (2013.01); *A61K 49/001* (2013.01); *A61K 49/0017* (2013.01); *A61K 49/0056* (2013.01); *A61K 51/065* (2013.01); *B82Y 5/00* (2013.01)

(58) Field of Classification Search

USPC ....................................... 424/178.1; 530/317

See application file for complete search history.

(56) References Cited

U.S. PATENT DOCUMENTS

| | | | | |
|---|---|---|---|---|
| 5,643,872 | A * | 7/1997 | Ali et al. | 424/94.64 |
| 2004/0042963 | A1 | 3/2004 | Katti et al. | |
| 2004/0043029 | A1 | 3/2004 | Hellstrom et al. | |
| 2006/0173161 | A1 * | 8/2006 | Kratz | 530/322 |
| 2010/0144647 | A1 * | 6/2010 | Kratz et al. | 514/18 |

FOREIGN PATENT DOCUMENTS

| | | | |
|---|---|---|---|
| DE | 219 771 | A5 | 3/1985 |
| EP | 1 738 770 | A1 | 1/2007 |
| WO | 99/55911 | A1 | 11/1999 |
| WO | 02/43771 | A2 | 6/2002 |
| WO | WO 02/43771 | A2 | 6/2002 |
| WO | WO 02/43771 | A3 | 6/2002 |
| WO | 02/074327 | A2 | 9/2002 |
| WO | WO 02/074327 | A2 | 9/2002 |
| WO | 02/085908 | A1 | 10/2002 |
| WO | WO 02/085908 | A1 | 10/2002 |
| WO | WO 02/094185 | A2 | 11/2002 |
| WO | 03/092742 | A1 | 11/2003 |
| WO | WO 03/092742 | A1 | 11/2003 |
| WO | 2004/062574 | A2 | 7/2004 |
| WO | WO 2004/062574 | A2 | 7/2004 |
| WO | 2004/087215 | A1 | 10/2004 |
| WO | 2004/091542 | A2 | 10/2004 |
| WO | WO 2004/087215 | A1 | 10/2004 |
| WO | WO 2004/091542 | A2 | 10/2004 |
| WO | 2004/098629 | A1 | 11/2004 |
| WO | WO 2004/098629 | A1 | 11/2004 |
| WO | WO 2005/019247 | A2 | 3/2005 |
| WO | 2005/051424 | A1 | 6/2005 |
| WO | WO 2005/092097 | A1 | 10/2005 |
| WO | WO 2005/110487 | A2 | 11/2005 |
| WO | 2006/092230 | A2 | 9/2006 |
| WO | WO 2006/092230 | A2 | 9/2006 |
| WO | 2006/104530 | A1 | 10/2006 |
| WO | WO 2006/104530 | A1 | 10/2006 |
| WO | 2007/022494 | A2 | 2/2007 |
| WO | WO 2007/022494 | A2 | 2/2007 |

OTHER PUBLICATIONS

NCBI-MeSH (Trifluoroacetic Acid, May 11, 2012).*

Temming et al. (Bioconjugate Chem., 2006, 17: 1385-1394).*

Bajusz, et al. "Highly potent metallopeptide analogues of luteinizing hormone-releasing hormone", *Proc. Natl. Acad. Sci.*, vol. 86, pp. 6313-6317, (1989).

Boturyn, et al. "Template Assembled Cyclopeptides as Multimeric System for Integrin Targeting and Endocytosis", *J. Am. Chem. Soc.*, vol. 126, pp. 5730-5739, (2004).

Chen, et al. "Synthesis and Biological Evaluation of Dimeric RGD Peptide-Paclitaxel Conjugate as a Model for Integrin-Targeted Drug Delivery", *J. Med. Chem.*, vol. 48, pp. 1098-1106, (2005).

David, et al. "Design of a multivalent galactoside ligand for selective targeting of HPMA copolymer-doxorubicin conjugates to human colon cancer cells", *Euro. J. of Cancer*, vol. 40, pp. 148-157, (2004).

Dharap, et al. "Molecular targeting of drug delivery systems to ovarian cancer by BH3 and LHRH peptides", *J. of Controlled Release*, vol. 91, pp. 61-73, (2003).

Dijkgraaf, et al. "Effects of linker variation on the in vitro and in vivo characteristics of an $^{111}$In-labeled RGD peptide", *Nuclear Medicine and Biology*, vol. 34, pp. 29-35, (2007).

(Continued)

*Primary Examiner* — Yan Xiao

(74) *Attorney, Agent, or Firm* — McDonnell Boehnen Hulbert & Berghoff LLP

(57) ABSTRACT

The present invention relates to a prodrug which comprises at least one pharmaceutically and/or diagnostically active compound bound by a cleavable linker, a receptor and/or antigen targeting moiety and a protein-binding moiety which is capable of binding to a carrier molecule.

9 Claims, 4 Drawing Sheets

(56) References Cited

OTHER PUBLICATIONS

Dijkgraaf, et al. "Improved targeting of the $\alpha_v\beta_3$integrin by multimerisation of RGD peptides", *Euro. J. of Nucl. Med. and Molec. Imag.*, vol. 34, No. 2, pp. 267-273, (2007).
Duncan, et al. "Polymer-drug conjugates, PDEPT and PELT: basic principles for design and transfer from the laboratory to clinic", *J. of Controlled Release*, vol. 74, pp. 135-146, (2001).
Eichler, et al. "Studies on the uptake of low molecular weight monomeric tris-galactosyl conjugates by the rat liver", *Biochem. Pharm.*, vol. 44, No. 11, pp. 2117-2122, (1992).
Fiume, et al. "Doxorubicin coupled to lactosaminated albumin inhibits the growth of hepatocellular carcinomas induced in rats by diethylnitrosamine", *J. of Hepatology*, vol. 43, pp. 645-652, (2005).
Garanger, et al. "Chemoselectively Addressable Template: A Valuable Tool for the Engineering of Molecular Conjugates", *J. Org. Chem.*, vol. 71, pp. 2402-2410, (2006).
de Groot, et al. "Design, Synthesis, and Biological Evaluation of a Dual Tumor-specific Motive Containing Integrin-targeted Plasmin-cleavable Doxorubicin Prodrug", *Molec. Can. Ther.*, vol. 1, pp. 901-911, (2002).
Hilgenbrink, et al. "Folate Receptor-Mediated Drug Targeting: From Therapeutics to Diagnostics", *J. of Pharm. Sci.*, vol. 94, No. 10, pp. 2135-2146, (2005).
Janaky, et al., "Short-chain analogs of luteinizing hormone-releasing hormone containing cytotoxic moieties", *Proc. Natl. Acad. Sci.*, vol. 89, pp. 10203-10207, (1992).
Janssen, et al., "Tumor Targeting with Radiolabeled $\alpha_v\beta_3$ Integrin Binding Peptides in a Nude Mouse Model", *Cancer Research*, vol. 62, pp. 6146-6151, (2002).
Kopeĉek, et al., "Water soluble polymers in tumor targeted delivery", *J. of Controlled Release*, vol. 74, pp. 147-158, (2001).
Koppán, et al., "Targeted Cytotoxic Analog of Luteinizing Hormone-Releasing Hormone AN-207 Inhibits the Growth of PC-82 Human Prostate Cancer in Nude Mice", *The Prostate*, vol. 38, pp. 151-158, (1999).
Leamon, et al., "Synthesis and Biological Evaluation of EC140: A Novel Folate-Targeted Vinca Alkaloid Conjugate", *Bioconjugate Chem.*, vol. 17, pp. 1226-1232, (2006).
Lee, et al., "Synthesis and Evaluation of Taxol-Folic Acid Conjugates as Targeted Antineoplastics", *Bioorg. & Med. Chem.*, vol. 10, pp. 2397-2414, (2002).
Lerchen, et al., "Anticancer activity of conjugates of camptothecin linked to $\alpha_v\beta_3$-ligands via people sequences which are cleaved by MMP-2", *Proc. Amer. Assoc. Cancer Res.*, vol. 43, #1234, (2002).
Lev-Goldman, et al., "Synthesis and Active Oxygen Generation by New Emodin Derivatives and Their Gonadotropin-Releasing Hormone Conjugates", *Bioconjugate Chem.*, vol. 17, No. 4, pp. 1008-1016, (2006).
Lim, et al., "The enhancement of liver targetability of [$^3$H]methotrexate-galactosylated serum albumin conjugate in mice", *Intl. J. of Pharm.*, vol. 132, pp. 175-182, (1996).
Liu, et al., "Effect of Coligands on Biodistribution Characteristics of Ternary Ligand $^{99m}$Tc Complexes of a HYNIC-Conjugated Cyclic RGDfK Dimer", *Bioconjugate Chem.*, vol. 16, No. 6, pp. 1580-1588, (2005).
Liu, et al., Impact of PKM Limkers on Biodistribution Characteristics of the $^{99m}$Tc-Labeled Cyclic RGDfK Dimer, *Bioconjugate Chem.*, vol. 17, No. 6, pp. 1499-1507, (2006).
Matulic-Adamic, et al., "Synthesis of *N*-Acetyl-D-galactosamine and Folic Acid Conjugated Ribozymes", *Bioconjugate Chem.*, vol. 13, No. 5, pp. 1071-1078, (2002).
Nagy, et al., "Selective coupling of methotrexate to peptide hormone carriers through a γ-carboxamide linkage of its glutamic acid moiety: Benzotriazol-1-yloxytris(dimethylamino)phosphonium hexafluorophosphate activation in salt coupling", *Proc. Natl. Acad. Sci.*, vol. 90, pp. 6373-6376, (1993).
Ohya, et al., "Synthesis and Cytotoxic Activity of Macromolecular Prodrug of Cisplatin Using Poly(ethylene glycol) with Galactose Residues or Antennary Galactose Units", *Macromol. Biosci.*, vol. 1, No. 8, pp. 355-363, (2001).
Ouchi, et al., "Design of attachment type of drug delivery system by complex formation of avidin with biotinyl drug model and biotinyl saccharide", *J. of Controlled Release*, vol. 94, No., pp. 281-291 (2004).
Pimm, et al., "Targeting of N-(2-Hydroxypropyl)Methacrylamide Copolymer-Doxorubicin Conjugate to the Hepatocyte Galactose-Receptor in Mice: Visualisation and Quantification by Gamma Scintigraphy as a Basis for Clinical Targeting Studies", *J. of Drug Target.*, vol. 1, pp. 125-131, (1993).
Rahimipour, et al., "Generation of Free Radicals by Emodic Acid and its [$_{D\text{-}Lys}{}^6$]GnRH-conjugate", *Photochem. and Photobio.*, vol. 74, No. 2, pp. 226-236, (2001).
Schally, et al., "Cancer chemotherapy based on targeting of cytotoxic peptide conjugates to their receptors on tumors", *Eur. J. of Endoc.*, vol. 141, pp. 1-14, (1999).
Temming, et al., "Evaluation of RGD-Targeted Albumin Carriers for Specific Delivery of Auristatin E to Tumor Blood Vessels", *Bioconjugate Chem.*, vol. 17, No. 6, pp. 1385-1394, (2006).
Thumshirn, et al., "Multimeric Cyclic RGD Peptides as Potential Tools for Tumor Targeting: Solid-Phase Peptide Synthesis and Chemoselective Oxime Ligation", *Chem. Eur. J.*, vol. 9, pp. 2717-2725, (2003).
Poethko, et al., "Two-step Methodology for High-Yield Routine Radiohalogenation of Peptides: $^{18}$F-Labeled RGD and Octreotide Analogs", *J. of Nucl. Med.*, vol. 45, No. 5, pp. 892-902, (2004).
Vlahov, et al., "Design and regioselective synthesis of a new generation of targeted chemotherapeutics. Part I: EC145, a folic acid conjugate of desacetylvinblastine monohydrazide", *Bioorg. & Med. Chem. Letters*, vol. 16, pp. 5093-5096, (2006).
Yang, et al., "Cytotoxic Activity of Gonadotropin-Releasing Hormone (GnRH)-Pokeweed Antiviral Protein Conjugates in Cell Lines Expressing GnRH Receptors", *Endocrinology*, vol. 144, No. 4, pp. 1456-1463, (2003).
Yoo, et al., "Folate-receptor-targeted delivery of doxorubicin nano-aggregates stabilized by doxorubicin-PEG-folate conjugate", *J. of Controlled Release*, vol. 100, pp. 247-256, (2004).
Bajusz, S., et al., "Highly Potent Metallopeptide Analogues of Luteinizing Hormone-Releasing Hormone", Proc. Natl. Acad. Sci, Aug. 1989, vol. 86(16), pp. 6313-6317.
Boturyn, D., et al., "Template Assembled Cyclopeptides as Multimeric System for Integrin Targeting and Endocytosis", J. Am. Chem. Soc, Jan. 6, 2004, vol. 126, pp. 5730-5739.
de Groot, F., et al., "Design, Synthesis, and Biological Evaluation of a Dual Tumor-Specific Motive Containing Integrin-Targeted Plasmin-Cleavable Doxorubicin Prodrug", Molecular Cancer Therapeutics, Sep. 2002, vol. 1, pp. 901-911.
Dharap, S.S., et al., "Molecular Targeting of Drug Delivery Systems to Ovarian Cancer by BH3 and LHRH Peptides", Journal of Controlled Release, 2003, vol. 91, pp. 61-73.
Dijkgraaf, I., et al., Effects of Linker Variation on the In Vitro and In Vivo Characteristics of an 111In-labeled RGD Peptide, Nuclear Medicine and Biology, 2007, vol. 34, pp. 29-35.
Dijkgraff, I., et al., "Improved Targeting of the avB3 Integrin by Multimerisation of RGD Peptides", European Journal of Nuclear Medicine and Molecular Imaging, Feb. 2007, vol. 34(2), pp. 267-273, DOI 10.1007/s00259-006-0180-9.
Garanger, E., et al., "Chemoselectively Addressable Template: A Valuable Tool for the Engineering of Molecular Conjugates", J. Org. Chem., 2006, vol. 71, pp. 2402-2410.
Hilgenbrink, A.R., et al., "Folate Receptor-Mediated Drug Targeting: From Therapeutics to Diagnostics", Journal of Pharmaceutical Sciences, Oct. 2005, vol. 94(10), pp. 2135-2146, DOI 10.1002/jps.20457.
Janaky, T., et al., "Short-Chain Analogs of Luteinizing Hormone-Releasing Hormone Containing Cytotoxic Moieties", Proc. Natl. Acad. Sci, Nov. 1992, vol. 89, pp. 10203-10207.
Janssen, M.I., et al., "Tumor Targeting with Radiolabeled avB3 Integrin Binding Peptides in a Nude Mouse Model", Cancer Research, Nov. 1, 2002, vol. 62, pp. 6146-6151.
Koppan, M., et al., "Targeted Cytotoxic Analog of Luteinizing Hormone-Releasing Hormone AN-207 Inhibits the Growth of PC-82 Human Prostate Cancer in Nude Mice", The Prostate, 1999, vol. 38, pp. 151-158.

(56) References Cited

OTHER PUBLICATIONS

Leamon, C.P., et al., "Synthesis and Biological Evaluation of EC140: A Novel Folate-Targeted Vinca Alkaloid Conjugate", Bioconjugate Chem, Aug. 19, 2006, vol. 17, pp. 1226-1232.
Lee, J, et al., "Synthesis and Evaluation of Taxol-Folic Acid Conjugates as Targeted Antineoplastics", Bioorganic & Medicinal Chemistry, 2002, vol. 10, pp. 2397-2414.
Lev-Goldman, V, et al., "Synthesis and Active Oxygen Generation by New Emodin Derivatives and their Gonadotropin-Releasing Hormone Conjugates", Bioconjugate Chem, Jul. 6, 2006, vol. 17, pp. 1008-1016.
Liu, S, et al, "Impact of PKM Linkers on Biodistribution Characteristics of the 99mTC-Labeled Cyclic RGDfK Dimer", Bioconjugate Chem, Nov. 1, 2006, vol. 17, pp. 1499-1507.
Liu, S, et al., "Effect of Coligands on Biodistribution Characteristics of Ternary Ligand 99mTc Complexes of a HYNIC-Conjugated Cyclic RGDfK Dimer", Bioconjugate Chem, Oct. 25, 2005, vol. 16, pp. 1580-1588.
Nagy, A., et al., "Selective Coupling of Methotrexate to Peptide Hormone Carriers Through a gamma-Carboxamide Linkage of its Glutamic Acid Moiety: Benzotriazol-1-yloxytris(dimethylamino)phosphonium Hexafluorophosphate Activation in Salt Coupling", Proc. Natl. Acad. Sci, Jul. 1993, vol. 90, pp. 6373-6376.
Ohya, Y, et al., "Synthesis and Cytotoxic Activity of Macromolecular Prodrug of Cisplatin Using Poly(ethylene glycol) with Galactose Residues or Antennary Galactose Units", Macromol. Biosci., 2001, vol. 1(8), pp. 355-363.
Poethko, T., et al., "Two-Step Methodology for High-Yield Routine Radiohalogenation of Peptide: 18F-Labeled RGD and Octreotide Analogs", The Journal of Nuclear Medicine, May 2004, vol. 45(5), pp. 892-902.
Rahimipour, S., et al., Generation of Free Radicals by Emodic Acid and its [d-Lys6]GnRH-Conjugate, Photochemistry and Photobiology, 2001, vol. 74(2), pp. 226-236.
Schally, A.V., et al., "Cancer Chemotherapy Based on Targeting of Cytotoxic Peptide Conjugates to their Receptors on Tumors", European Journal of Endocrinology, 1999, vol. 141, pp. 1-14.
Sivolapenko, G.B., et al., "Breast Cancer Imaging with Radiolabelled Peptide from Complementarity-Determining Region of Antitumour Antibody", Lancet, 1995, vol. 346, pp. 1662-1666.
Temming, K., et al., "Evaluation of RGD-Targeted Albumin Carriers for Specific Delivery of Auristatin E to Tumor Blood Vessels", Bioconjugate Chem., 2006, vol. 17, pp. 1385-1394.
Thumshirn, G., et al., "Multimeric Cyclic RGD Peptides as Potential Tools for Tumor Targeting: Solid-Phase Peptide Synthesis and Chemoselective Oxime Ligation", Chem. Eur. J., 2003, vol. 9, pp. 2717-2725, DOI:10.1002/chem.200204304.
Vlahov, I.R., et al., "Design and Regioselective Synthesis of a New Generation of Targeted Chemotherapeutics. Part 1: EC145, a Folic Acid Conjugate of Desacetylvinblastine Monohydrazide", Bioorganic & Medicinal Chemistry Letters, 2006, vol. 16, pp. 5093-5096.
Yang, W., et al, "Cytotoxic Activity of Gonadotropin-Releasing Hormone (GnRH)-Pokeweed Antiviral Protein Conjugates in Cell Lines Expressing GnRH Receptors", Endocrinology, 2003, vol. 144(4), pp. 1456-1463, doi:10.1210/en.2002-220917.
Yoo, H.S., et al., "Folate-Receptor-Targeted Delivery of Doxorubicin Nano-Aggregates Stablized by Doxorubicin-PEG-Folate Conjugate", Journal of Controlled Release, 2004, vol. 100, pp. 247-256.

* cited by examiner

RECEPTOR AND ANTIGEN TARGETED PRODRUG

The present invention relates to a prodrug which comprises at least one pharmaceutically and/or diagnostically active compound bound by a cleavable linker, a receptor and/or antigen targeting moiety and a protein-binding moiety which is capable of binding to a carrier molecule.

Most of the drugs used at present are compounds having low-molecular weights and exhibit, when systemically administered to a patient, a high plasma clearance or total body clearance. Furthermore, said low-molecular weight compounds show a high tendency to penetrate body tissues by diffusion, resulting in a uniform biodistribution. These are the two main reasons why only small quantities of the drug reach the site of action and, due to distribution over healthy tissues of the body, said drugs give rise to problematic side-effects. These disadvantages are of particular concern for those drugs having a high cytotoxic potential, such as cytotoxic agents, immunosuppressive agents or virostatic agents.

Several strategies have been pursued for improving the selectivity of low-molecular weight drugs and thus to increase the concentration of the active agent in the desired tissue, while the concentration of the same is decreased in healthy tissues in order to reduce side-effects.

Carriers, such as for example albumin, or its drug conjugates exhibit a markedly long half-life in the systemic circulation of up to 19 days (cf. Peters, T. J., "Serum Albumin", *Adv. Protein. Chem.,* 1985, 37, 161-245). Because of an elevated permeability of vessel walls of the e.g. malignant, infected or inflamed tissue for macromolecules, the carrier, such as for example serum albumin, passes preferentially into the target tissue thus achieving a so-called passive targeting effect (cf. Maeda, H., Mastumura, Y., *Crit. Rev. Ther. Drug Carrier Sys.,* 1989, 6, 193-210). The drugs can be bound to exogenous or endogenous albumin (DE 103 10 082 A1, DE 10 2005 009 084 A1, PCT/EP00/05272, PCT/EP00/05254).

Apart from such passive targeting, it is desirable to actively target a certain tissue of interest, for which e.g. tumor-associated receptors and antigens have been envisaged as molecular targets, which can be recognized by specific monoclonal antibodies. Since the discovery of a preparation method for monoclonal antibodies by Milstein and Köhler in 1975, a variety of antibodies has been developed of which some show improved tumor selectivity. However, antibody-drug-conjugates have not been proven to be clinically successful although intensive efforts have been invested in that field over the past 20 years. Moreover, disadvantages such as difficult and cost-intensive preparation and ineffective drug transport due to their high molecular weight (~150 kDa) have not yet been overcome.

Therefore, a need exists for improved drugs which enable the treatment and/or diagnosis of a disease in a patient, and which avoid or at least reduce the above-described disadvantages.

In view of the above, the technical problem underlying the present invention is to provide novel prodrugs, which should combine passive and active targeting, and which should therefore have a high selectivity and thus improved therapeutic and/or diagnostic properties.

According to the present invention, the above-described technical problem is solved by providing a prodrug comprising (i) at least one pharmaceutically and/or diagnostically active compound,
(ii) at least one receptor and/or antigen targeting moiety,
(iii) at least one cleavable linker, and
(iv) a protein-binding moiety, wherein the pharmaceutically and/or diagnostically active compound is bound to a cleavable linker.

According to the present invention, there is no specific restriction as to how the components, i.e. the pharmaceutically and/or diagnostically active compound, the receptor and/or antigen targeting moiety, the cleavable linker and the protein-binding moiety of the above-defined prodrug are connected to each other, as long as the pharmaceutically and/or diagnostically active compound is bound to a cleavable linker and the biological function of the protein-binding moiety and the pharmaceutically and/or diagnostically active compound is not negatively affected by the structure set up. The molecular structure of the prodrug of the present invention may for example have a linear form or a branched form or is present in a circular form.

According to the present invention, there is no specific restriction concerning the structural setup of the prodrug of the present invention; i.e. the way the constituents as outlined under above items (i) to (iv) of the above-defined prodrug are chemically bonded together. In particular, the prodrug according to the present invention may contain one or more spacers in any position between the constituents of the above-defined prodrug, i.e. the protein-binding moiety may for example be bound to the rest of the prodrug through a spacer or, as another example, the first pharmaceutically and/or diagnostically active compound may be bound to at least one cleavable linker through a spacer. Furthermore, the function of e.g. the cleavable linker may be incorporated in such a spacer, i.e. a spacer may be used between the pharmaceutical and/or diagnostically active compound which can also serve as the cleavable linker. It is also possible to bind the pharmaceutically and/or diagnostically active compound, the cleavable linker, and/or the protein-binding moiety to a central group, which may be linear or branched, such as a peptide, a sugar, a heterocyclic group, or any inorganic or organic compound suitable to bind one or more of the constituents of the prodrug.

The term "prodrug" as used herein means any form of a drug which is administered to an organism, such as a human, in an inactive or less active form and is converted, e.g. by metabolization, into the active form. Said conversion of the prodrug into the active form is not specifically restricted and includes any chemical and/or physical alteration of the prodrug which occurs after administration, such as for example release of an active part of the prodrug at the site of action.

The expression "pharmaceutically active compound" means any compound which brings about a pharmacological effect either by itself or after its conversion in the organism in question, and thus also includes the derivatives from these conversions. The pharmacological effect of the pharmaceutically active compound according of the present invention can be a single effect only, e.g. a cytostatic effect, or a broad pharmacological spectrum of action, such as an immunosuppressive and antiphlogistic effect at the same time.

The expression "diagnostically active compound" used herein is not specifically restricted and includes any compound which can be detected and preferably quantified, in an organism or parts thereof, such as for example cells and/or fluids, such as for example the serum, through suitable chemical and/or physical measurement methods.

The expression "receptor and/or antigen targeting moiety", which may be also designated as ligand(s), used herein is not specifically restricted and means any chemical group or compound which is able to interact with a desired receptor or antigen. The receptor and/or antigen targeting moiety preferably interacts with the receptor or antigen by physically and/or chemically binding to it as a ligand.

Especially preferred receptors and/or antigens that are targeted by the ligand of the prodrug as defined above are such receptors and/or antigens which are upregulated or exclusively expressed in tissues associated with a disease, such as for example in malignant tissue of a tumor.

Especially preferred examples of such receptors are receptors of growth factors, of vitamins, of cytokines, of hormones, of peptides, of plasma proteins, of the endothelium, or G-protein coupled receptors. Especially preferred examples of antigens are those associated with cancer and inflammatory diseases.

The expression "cleavable linker" means any linker which can be cleaved physically or chemically. Examples for physical cleavage may be cleavage by light, radioactive emission or heat, while examples for chemical cleavage include cleavage by redox-reactions, hydrolysis, pH-dependent cleavage or cleavage by enzymes.

According to a preferred embodiment of the present invention, the cleavable linker comprises one or more hydrolytically cleavable bonds, the hydrolysis of which releases the pharmaceutically and/or diagnostically active compounds. Examples for hydrolytically cleavable bonds are ester bonds or metal-complex bonds, such as are present in platinum-dicarboxylate complexes, where a diaminediaquoplatinum (II) complex is liberated.

In another preferred embodiment of the present invention, the cleavable linker may be cleavable by an enzyme. For example, the cleavable linker of the present invention may contain at least one peptide bond which preferably lies within a cleavable peptide sequence of a protease. A peptide bond can therefore be implemented by the insertion of a respective peptide sequence into the cleavable linker. Suitable enzymes are, for example, proteases and peptidases, e,g. matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. Preferred examples of proteases according to the present invention are in particular MMP-2, MMP-3 and MMP-9, cathepsin B, H, L and D, plasmin, urokinase, and prostate-specific antigen (PSA). Preferred peptide sequences that are incorporated in the prodrug are: Arg, Arg-Arg, Phe-Arg, Phe-Cit, Ile-Pro Lys, Lys-Lys, Arg-Lys, Ala-Leu-Ala-Leu (SEQ ID NO: 2), Phe-Lys, Phe-Lys-Ala, Val-Cit, Val-Arg, Ala-Phe-Lys, D-Ala-Phe-Lys, Met, Met-Met, Phe-Met, Tyr-Met, Ala-Met, Ala-Phe-Met, Phe-Ala-Met, Ala-Tyr-Met, Phe-Tyr-Met, Ser-Ser-Tyr-Tyr-Ser-Arg (SEQ ID NO: 3), Phe-Pro-Lys-Phe-Phe-Ser-Arg-Gln (SEQ ID NO: 4), Lys-Pro-Ile-Glu-Phe-Nph-Arg-Leu (SEQ ID NO: 5), Gly-Pro-Leu-Gly-Ile-Ala-Gly-Gln (SEQ ID NO: 6), Gly-Pro-Leu-Gly-Ile-Ala-Gly-Gln (SEQ ID NO: 6), Gly-Pro-Gln-Gly-Ile-Trp-Gly-Gln (SEQ ID NO: 7), Gly-Phe-Leu-Gly (SEQ ID NO: 8). In addition, the enzymatically cleavable linker may contain a self-immolative linker such as a self-immolative p-aminobenzyloxycarbonyl (PABC) linker or a N-methyl- or symmetric N,Ndimethylethylene linker.

In another embodiment of the present invention, the cleavable linker according to the present invention preferably contains at least one acid-labile bond. Examples of acid-labile bonds are ester, acetal, ketal, imine, hydrazone, carboxylhydrazone and sulfonylhydrazone bonds and bonds containing a trityl group.

According to the present invention, in case the pharmaceutically and/or diagnostically active compound is a diagnostically active agent which does not need to be cleaved, the cleavable linker may be chosen to comprise only such bonds which are difficult to cleave under physiological conditions such as an amide bond, carbon-carbon bonds or bonds between carbon and a heretoratom, wherein the heteroatom may be selected from O, N, S or P.

The term "protein-binding moiety" used herein is not specifically restricted and means any functional group which is capable of binding to an amino, a hydroxy or thiol group of a carrier molecule which may be of endogenous or exogenous origin. Examples of a protein-binding moiety according to the present invention are a maleinimide group, a halogenacetamide group, a halogenacetate group, a pyridylthio group, a vinylcarbonyl group, an aziridin group, a disulfide group, a substituted or unsubstituted acetylene group, a hydroxysuccinimide ester group.

The protein-binding group also includes functional groups, such as —COOH or $SO_3H$, that can be activated by standard coupling agents, e.g. dicyclocarbodiimides, acid chlorides, or peptide coupling reagents (e.g., BOP, HATU, PyBOP).

One or several prodrugs can be bound to any suitable carrier such as peptides, sugars, serum proteins, antibodies or antibody fragments, polysaccharides, or synthetic polymers. The carrier in general contains suitable functional groups such as hydroxy, amino or thiol groups to bind the protein-binding prodrug. If necessary, these can be introduced in the carrier molecule by chemical modification through techniques known to those skilled in the art (Kratz et al., (2001): Anticancer drug conjugates with macromolecular carriers, in Polymeric Biomaterials, second edition, ed. S. Dumitriu, Marcel Dekker, New York, Chapter 32, 851-894).

In a preferred embodiment, the protein-binding moiety of the prodrug according to the present invention allows said prodrug to bind in situ after administration by e.g. injection, to components of body fluids and/or tissue components, preferably to serum proteins and more preferably to serum albumin, particularly to cysteine-34 of serum albumin and are then present as macromolecular prodrugs which carry the pharmaceutically and/or diagnostically active compounds to the target site.

In a further preferred embodiment, the protein-binding moiety of the above-defined prodrug binds in situ to cysteine-34 of albumin.

According to the present invention, the term "in situ" includes the binding of the prodrug according to the present invention to an endogenous biomolecule, such as a serum protein, particularly serum albumin, inside the organism to which the prodrug has been administered.

According to another embodiment of the present invention, the pharmaceutically and/or diagnostically active compound of the above-defined prodrug is selected from the group consisting of a cytostatic agent, a cytokine, an immunosuppressant, an antirheumatic, an antiphlogistic, an antibiotic, an analgesic, a virostatic, and an antimycotic agent, a transcription factor inhibitor, a cell cycle modulator, a MDR modulator, a proteasome or protease inhibitor, an apoptosis modulator, an enzyme inhibitor, an angiogenesis inhibitor, a hormone or hormone derivative, a radioactive substance, a light emitting substance, and a light absorbing substance.

Especially suitable cytostatic agents according to the present invention are the N-nitrosoureas such as nimustine, the anthracyclines doxorubicin, daunorubicin, epirubicin, idarubicin, mitoxantrone and ametantrone, and any derivatives thereof such as 2-pyrollinoanthracyclines, morpholinoanthracyclines, diacetatoxyalkylanthracyclines; the alkylating agents chlorambucil, bendamustine, melphalan, and oxazaphosphorines, and any derivatives thereof; the antimetabolites, for example purine antagonists or pyrimidin antagonists, such as 5-fluorouracil, 2'-deoxy-5-fluorouridine, cytarabine, cladribine, fludarabine, pentostatine, gemcitabine and thioguanine, and any derivatives thereof; folic acid antagonists such as methotrexate, raltitrexed, pemetrexed and plevitrexed, the taxanes paclitaxel and docetaxel, and any derivatives thereof; the camptothecins topotecan, irinotecan, 9-aminocamptothecin and camptothecin, and any derivatives thereof; the Vinca alkaloids vinblastine, vincristine, vindesine and vinorelbine, and any derivatives thereof; calicheamicins and any derivatives thereof; maytansinoids and any derivatives thereof; auristatins and any derivatives thereof; epothilones and any derivatives thereof; bleomycin, dactinomycin, plicamycin, mitomycin C and cis-configured platinum(II) complexes.

Especially suitable cytokines according to the present invention are, for example, interleukin 2, interferon α-2a, interferon α-2b, interferon β-1a, interferon β-1b, interferon γ-1b, tumor necrosis factor, and any derivatives thereof.

Especially suitable immunosuppressants according to the present invention are, for example, cyclosporin A, tacrolimus, sirolimus, everolimus, mycophenolatmofetil, and any derivatives thereof.

Especially suitable antirheumatics according to the present invention are, for example, methotrexate, leflunomid, sulfasalazine, chloroquine, and any derivatives thereof.

Especially suitable antiphlogistics and/or analgesics according to the present invention are, for example, salicylic acid derivatives such as for example acetylsalicylic acid, and any derivatives thereof; drug derivatives having an acetic or propionic acid group such as diclofenac or, respectively, naproxen, and aminophenol derivatives such as for example paracetamol.

Especially preferred antibiotics according to the present invention are, for example, sulfanilamide, sulfacarbamide and sulfamethoxydiazine, and any derivatives thereof; penicillins, for example 6-aminopenicillanic acid, penicillin G as well as penicillin V, and any derivatives thereof; isoxazolylpenicillins such as oxacillin, cloxacillin and clucloxacillin, and any derivatives thereof; α-substituted benzylpenicillins such as ampicillin, carbenicillin, pivampicillin, amoxicillin, and any derivatives thereof; acylaminopenicillins, for example mezlocillin, azlocillin, piperacillin, apalcillin and any derivatives thereof; amidinopenicillins, for example mecillinam; atypical β-lactams such as imipenam and aztreonam; cephalosporins, for example cephalexin, cefradin, cefaclor, cefadroxil, cefixime, cefpodoxime, cefazolin, cefazedone, cefuroxime, cefamandole, cefotiam, cefoxitin, cefotetan, cefmetazole, latamoxef, cefotaxmine, ceftriaxone, ceftizoxime, cefmonoxime, ceftazidime, cefsulodin and cefoperazone, and any derivatives thereof; tetracyclines such as tetracycline, chlorotetracycline, oxytetracycline, demeclocycline, rolitetracycline, doxycycline, minocycline, and any derivatives thereof; chloramphenicols such as chloramphenicol and thiamphenicol, and any derivatives thereof; gyrase inhibitors, for example nalidixic acid, pipemidic acid, norfloxacin, ofloxacin, ciprofloxacin and enoxacin, and any derivatives thereof; and antituberculotics such as isoniazid, and any derivatives thereof.

Especially preferred virostatics according to the present invention are, for example nucleoside analogs such as acyclovir, ganciclovir, idoxuridine, ribavirin, vidaribine, zidovudine, didanosine and 2',3'-dideoxycytidine (ddC), and any derivatives thereof, as well as amantadine.

Especially suitable antimycotic agents according to the present invention are, for example, amphotericin B, and any derivatives thereof.

Especially preferred transcription factor inhibitors according to the present invention are, for example compounds that inhibit activation of NF-κB such as curcumin (diferuloylmethane) epigallocatechin-3-gallate (EGCG; green tea polyphenols), phenanthrolines, pyrrolinedithiocarbamate (PDTC), quercetin, tepoxaline (5-(4-chlorophenyl)-N-hydroxy-(4-methoxyphenyl)-N-methyl-1H-pyrazole-3-propanamide), PMC (2,2,5,7,8-pentamethyl-6-hydroxychromane), benzylsocyanate, resveratol, genistein, lupeol, lycopene, panepoxydone, epoxyquinomicin C, dehydroxymethylepoxyquinomicin (DHMEQ), cycloepoxydon, gliotoxin, as well as I-κB-alpha phosphorylation and/or degradation inhibitors such as PS-1,145, BAY-11-7082 (E3[(4-methylphenyl)-sulfonyl]-2-propenenitrile), BAY-11-7085 (E3[(4-t-butylphenyl)-sulfonyl]-2-propenenitrile), cycloepoxydon; 1-hydroxy-2-hydroxymethyl-3-pent-1-enylbenzene, sanguinarine (pseudochelerythrine, 13-methyl-[1,3]-benzodioxolo-[5,6-c]-1,3-dioxolo-4,5 phenanthridinium), sulfasalazine, capsaicin (8-methyl-N-vanillyl-6-nonenamide), emodin (3-methyl-1,6,8-trihydroxyanthraquinone), erbstatin (tyrosine kinase inhibitor), estrogen (E2), gliotoxin, genistein, resiniferatoxin, and miscellaneous inhibitors of NF-κB such as beta-amyloid protein, glucocorticoids (dexamethasone, prednisone, methylprednisolone), leptomycin B (LMB), O,O'-bismyristoyl thiamine disulfide (BMT), ADP ribosylation inhibitors e.g., bi-, tri, or tetracyclic lactames, 1,8-naphtalimide derivatives, phenanthridin-6-ones, 3,4-dihydro-5-methyl-isoquinolin-1(2H)-one, benzoxazole-4-carboxamide, 1,6-naphthyridine-5(6H)-ones, quinazolin[3,4-d]pyrimidin-4(3H)-ones, 1,5-dihydroxyisoquinoline, 2-methyl-quinazolin-4[3H]-ones, 1,11b-dihydro-[2H]benzopyrano[4,3,2-de]isoquinolin-3-one, atrial natriuretic peptide (ANP), atrovastatin (HMG-CoA reductase inhibitor), calcitriol (1a,25-dihydroxyvitamine D3), E3330 (quinone derivative), herbimycin A, hypericin, hydroquinone (HQ), KT-90 (morphine synthetic derivatives), mevinolin, 5'-methylthioadenosine (MTA), pentoxifylline (1-(5'-oxohexyl) 3,7-dimethylxanthine, PTX), phenyl-N-tert-butylnitrone (PBN), pituitary adenylate cyclase-activating polypeptide (PACAP), quinadril (ACE inhibitor), ribavirin, secretory leukocyte protease inhibitor (SLPI), serotonin derivative (N-(p-coumaroyl) serotonin, silymarin, vasoactive intestinal peptide (VIP), D609 (phosphatidylcholine-phospholipase C inhibitor), RO31-8220 (PKC inhibitor), SB203580 (p38 MAPK inhibitor), triptolide (PG490, extract of Chinese herb), LY294,002, mesalamine, wortmannin (fungal metabolite), or CHS 828 (N-(6-(p-chlorophenoxy)-hexyl)-N'-cyano-N"-4-pyridylguanidine), sesquiterpene lactones such as parthenoilde, helenalin, miller-9E-enolid and budlein A.

Especially preferred proteasome and protease inhibitors according to the present invention are, for example peptide aldehydes: ALLnL (N-acetyl-leucinyl-leucynil-norleucynal, MG101), LLM (N-acetyl-leucinyl-leucynil-methional), Z-LLnV (carbobenzoxy)-leucinyl-leucynil-norvalinal, MG115), Z-LLL (carbobenzoxyl-leucinyl-leucynil-leucynal, MG132), boronic acid derivatives, e.g. PS-273, PS-293, PS-296, PS-303, PS-305, PS-313, PS-321, PS-325, PS-334, PS-341, PS-364, PS-352, PS-383, lactacystine, beta-lactone, boronic acid peptide, ubiquitin ligase inhibitors deoxyspergualin, APNE (N-acetyl-DL-phenylalanine-beta-naphthylester), BTEE (N-benzoyl L-tyrosine-ethylester), DCIC (3,4-dichloroisocoumarin), DFP (diisopropyl-uorophosphate), TPCK (N-alpha-tosyl-L-phenylalanine chloromethyl ketone), TLCK (N-alpha-tosyl-L-lysine chloromethyl ketone).

Especially preferred apoptosis modulators according to the present invention are, for example farnesyl transferase inhibitors, e.g. R115777, SCH66336, BMS214662, Imatinib, 17-AAG, EGFR inhibitors, e.g., ZD1839, ZD647, BIBW 2992, or erlotinib, MEK inhibitors, e.g., PD 032590, RAF inhibitors e.g., BAY43-9006, PKC inhibitors, e.g. UCN-01, PKC-412, Bryostatin, ISIS-3521, LY333531, safingol, CGP-41251 (midostaurin), HDAC inhibitors, e.g., suberoyl-3-aminopyridineamide hydroxamic acid, lonidamine, apoptin, survivin, rapamycin, CCI-779, RAD001 (everolimus), PXD101, tyrosine kinase inhibitors, e.g. Iressa, OSI-774, STI-571, inhibitors of enzymes in the mitogen-activated protein kinase pathway e.g., PD-098059, U-0126.

Especially preferred cell cycle modulators according to the present invention are, for example flavopiridol, bryostain-1, roscovitine, BMS-387032, perifosine, or lovastatin.

Especially preferred angiogenesis inhibitors according to the present invention are, for example thalidomide, endostatin, celecoxib, ABT-510, combrestatin A4, dalteparin, dimethylxanthenone acetic acid, lenalidomide, LY317615 (enzastaurin), PPI-2458, ADH-1 (exherin), AG-013736, AMG-706, AZD2171, Bay 43-9006 (sorafenib), BMS-582664, CHIR-265, GW786034 (pazopanib), PI-88, PTK787/ZK 222584 (vatalanib), RAD001 (everolimus), SU11248 (sunitinib), suramin, XL184, ZD6474, ATN-161, or EMD 121974 (cilenigtide).

Especially preferred hormones or hormone derivatives according to the present invention are, for example aminogluthemid, buserilin, cyproteronacetate, droloxifen, ethinylestradiol, flutamid, formesta, fosfestrol, gestonoroncaproate, goserilin, leuprolein, lynestrenol, medrogeston, medroxyprogesteronacetate, megestrolactetate, octreotid, tamoxifen, toremifin, triptorelin, anastrazole, exemestane, or letrozole.

For preparing the prodrugs of the present invention the pharmaceutically and/or diagnostically active compounds are bound to a bifunctional protein-binding linker through an acid-sensitive or hydrolytically or enzymatically cleavable bond. This derivatisation is carried out with a suitable functional group of the pharmaceutically and/or diagnostically active compound which is a HO—, $NH_2$—, HOOC—, $HO_3S$—, or carbonyl group. If the first and second pharmaceutically and/or diagnostically active compound does not contain a suitable functional group, then this is introduced through chemical modification; i.e. the above-mentioned first and second pharmaceutically and/or diagnostically active compounds additionally include all derivatives that possess a HO—, $NH_2$—, HOOC—, $HO_3S$—, and/or carbonyl group.

In a preferred embodiment, the pharmaceutically and/or diagnostically active compound of the above-defined prodrug is a cytostatic selected from the group consisting of anthracyclines, N-nitrosoureas, alkylating agents, purin- or pyrimidin antagonists, folic acid antagonists, taxanes, camptothecines, podophyllotoxin derivatives, vinca-alkaloids, calicheamicines, maytansinoids, epothilones, auristatins and cis-configured platinum(II)-complexes.

The receptor and/or antigen targeting moiety is a ligand that interacts with a disease-related receptor or antigen such as growth factor receptors, e.g. the transferrin receptor, receptors for EGFR (ErbB-1), Her2/c-neu (ErbB-2), Her 3 (ErbB-3) and Her 4 (ErbB-4), transforming growth factor receptor (TGF), platelet derived growth factor receptor (PDGF), hepatocyte growth factor receptor, fibroblast growth factor (FGF), receptors for cytokines such as for interleukin, interleukin 2, interferon α-2a, interferon α-2b, interferon β-1a, interferon β-1b, interferon γ-1b, tumor necrosis factor, and any derivatives thereof; peptide receptors such as for somatostatin, vasoactive intestinales peptide (VIP), luteinising hormone-releasing hormone (LHRH), bombesin (BN), gastrin-releasing-peptide (GRP), cholecystokinin (CCK), substance P (SP), neurotensin (NT), neuropeptide Y (NPY), α-melanocyte stimulating hormone (α-MSH), vitamin receptors such as the folate receptor, folate reduced carrier, vitamin D receptors, retinoid binding proteins, cabalamin binding proteins and their receptors, riboflavin carrier proteins, binding proteins for tocopherol, ascorbic acid, thiamine and vitamin, biotin binding proteins, vascular receptors such as vascular endothelial growth factor receptors (VEGFR-1/VEGFR-2), integrins, e.g. αvβ3, αvβ5, α5β1, Tie-2, CD44 receptor, aminopeptidase N, aminopeptidase P, NG2 proteoglycan, ED-B, vessel marker for LyP-1, endothelial leucocyte cell adhesion molecule-1 (E-selectin), vascular cell adhesion molecule-1 (VCAM-1), eridoglin, E-cadherin, receptors such as the asialoglycoprotein receptor, scavenging receptors and the LDL receptor, apoptosis-inducing tumor necrosis factor (TNF) family receptors, Fas receptor (CD95), TRAIL receptors (TRAIL-R1, TRAIL-R2, TRAIL-R3 and TRAIL-R4), CanAg receptor, N-cadherin, or antigens such as carcinoembryonic antigen (CEA), tissue polypeptide antigen (TPA), colon-specific antigen-p, prostate-specific membrane antigen (PSMA) CA 19-9, CA 15.3, CA 72-4, CA 50; CA 125, CA 195, DuPAN-2, SCC-A/Ta-4, SP 4, Ly-2.1, L6, SL-2Ly, Ely-Ly, Lewis-Y, Ki-67 antigen, SART3 tumor antigen, MCA and other breast cancer associated mucinous glycoproteins, CD1 to CD150, especially CD4, CD8, CD19, CD20, CD21, CD22, CD29, CD33, CD44, CD46, CD55, CD56, CD59, CD 63, CD87 and CD95.

Another embodiment of the present invention relates to the prodrug as defined above, wherein the receptor and/or antigen targeting moiety is derived from a peptide, a peptidomimetic, a sugar, a vitamin or a lipid. The ligand attached to the prodrug can contain one or more of said molecules that are connected in a linear, cyclic and/or branched manner.

According to a preferred embodiment, the receptor and/or antigen moiety of the above-defined prodrug comprises a folic acid derivative.

According to another preferred embodiment, the receptor and/or antigen moiety of the above-defined prodrug comprises a sugar cluster, for example a Gal- and/or GalNAc-cluster.

According to another preferred embodiment, the receptor and/or antigen moiety of the above-defined prodrug comprises one or more peptide derivatives, for example, SPLWRNSVL (SEQ ID NO: 9), TSPLNIHNGQKL (SEQ ID NO: 10), MYWGDSHWLQYWYE (SEQ ID NO: 11), MCPKHPLGC (SEQ ID NO: 12), HLQIQPWYPQIS (SEQ ID NO: 13), HEWSYLAPYPWF (SEQ ID NO: 14), KCCYSL (SEQ ID NO: 15), CESLWGGLMWTIGLSDC (SEQ ID NO: 16), CNIWGVVLSWIGVFPEC (SEQ ID NO: 17), LTVGPWG (SEQ ID NO: 18), CDRGDCFC (RGD-4C) (SEQ ID NO: 19), ACDCRGDCFCG (SEQ ID NO: 20), CNGRCVSGCAGRC (SEQ ID NO: 21), CVCNGRMEC (SEQ ID NO: 22), NGRAHA (SEQ ID NO: 23), CGSLVRC (SEQ ID NO: 24), CGLSDSC (SEQ ID NO: 25), TAASGVRSMH (SEQ ID NO: 26), LTLRWVGLMS (SEQ ID NO: 27), CTTHWGFTLC (SEQ ID NO: 28), NRSLKRISNKRIRRK (SEQ ID NO: 29), RRKRRR (SEQ ID NO: 30), ATWLPPR (SEQ ID NO: 31), CPGPEGAGC (SEQ ID NO: 32), SMSIARL (SEQ ID NO: 33), VSFLEYR (SEQ ID NO: 34), PRPGAPLAGSWPGTS (SEQ ID NO: 35), DRWRPALPVVLFPLH (SEQ ID NO: 36), ASSSYPLIHWRPWAR (SEQ ID NO: 37), HTMYYHHYQHHL (SEQ ID NO: 38), CGNKRTRGC (SEQ ID NO: 39), CGNRTRGC (SEQ ID NO: 40), NGEIEWYSWVTHGMY (SEQ ID NO: 41), CCDRGDCFC (SEQ ID NO: 42), CCNGRC (SEQ ID NO:

43), cCGNKRTRGC (SEQ ID NO: 44), cCGFECVRQC-PERC (SEQ ID NO: 45), or $[c(RGDF)]_2$(SEQ ID NO: 46).

According to another preferred embodiment, the receptor and/or antigen targeting moiety of the above-defined prodrug comprises one or more cyclic peptide derivatives comprising the sequence $[c(RGDF)]_2$.

According to another preferred embodiment, the receptor and/or antigen targeting moiety of the above-defined prodrug comprises one or more peptide derivatives comprising the sequence (Pyr)-His-Trp-Ser-Tyr-Lys-Leu-Arg-Pro-Gyl-$NH_2$ ($[Lys^6]$-LHRH).

According to a preferred embodiment the receptor and/or antigen targeting moiety of the above-defined prodrug comprises one or more peptides that are derived from a complementarity-determining region (CDR) from an antibody that interacts with a disease-specific or disease-related antigen. Said peptides can be linear, branched or cyclic in nature and typically contain 5-100 amino acids, preferably 5-40 amino acids.

The above-mentioned peptide derivatives can contain L- or D-amino acids.

In another embodiment of the present invention, the cleavable linker of the above-defined prodrug can be cleaved hydrolytically and/or enzymatically and/or pH-dependently.

According to a further embodiment, the protein-binding moiety of the above-defined prodrug is selected from the group consisting of a maleinimide group, a halogenacetamide group, a halogenacetate group, a pyridylthio group, a vinylcarbonyl group, an aziridin group, a disulfide group, a substituted or unsubstituted acetylene group, and a hydroxysuccinimide ester group.

The protein-binding group also includes functional groups, such as —COOH or $SO_3H$, that can be activated by standard coupling agents, e.g. dicyclocabodiimides, acid chlorides, or peptide coupling reagents (e.g., BOP, HATU, PyBOP).

According to another embodiment of the present invention, the pharmaceutically and/or diagnostically active compound of the prodrug as defined above contains one or more radionuclides, one or more positron emitters, one or more NMR contrast agents, one or more fluorescent compound(s), or one or more near-infrared contrast agents.

According to another specific embodiment of the present invention, the prodrug as defined above comprises (i) 2-pyrollinodoxorubicin, morpholinodoxorubicin, diacetatoxypentyldoxorubicin, doxorubicin, paclitaxel, camptothecin, or a derivative thereof, (ii) a receptor group selected from the group consisting of cyclic $[c(RGDF)]_2$-peptides, (iii) at least one cleavable linker, selected from the group consisting of an acid-labile linker and a linker cleavable by MMP2 and/or MMP9, and (iv) a maleinimide or a derivative thereof as the protein-binding moiety, wherein 2-pyrollinodoxorubicin, morpholinodoxorubicin, diacetatoxypentyldoxorubicin, doxorubicin, paclitaxel or camptothecin, or the derivative thereof is bound to the at least one cleavable linker.

According to another specific embodiment of the present invention, the prodrug as defined above comprises (i) 2-pyrollinodoxorubicin, morpholinodoxorubicin, diacetatoxypentyldoxorubicin, doxorubicin, paclitaxel, camptothecin, or a derivative thereof, (ii) a receptor group selected from the group consisting of sugar clusters, (iii) at least one cleavable linker selected from the group consisting of acid-labile linkers, (iv) a maleinimide or a derivative thereof as the protein-binding moiety, wherein 2-pyrollinodoxorubicin, morpholinodoxorubicin, diacetatoxypentyldoxorubicin, doxorubicin, paclitaxel or camptothecin, or the derivative thereof is bound to the at least one cleavable linker.

According to another specific embodiment of the present invention, the prodrug as defined above comprises (i) 2-pyrollinodoxorubicin, morpholinodoxorubicin, diacetatoxypentyldoxorubicin, doxorubicin, paclitaxel, camptothecin, or a derivative thereof, (ii) a receptor group selected from the group consisting of a Gal- and GalNAc-cluster, (iii) at least one cleavable linker selected from the group consisting of acid-labile linkers, (iv) a maleinimide or a derivative thereof as the protein-binding moiety, wherein 2-pyrollinodoxorubicin, morpholinodoxorubicin, diacetatoxypentyldoxorubicin, doxorubicin, paclitaxel or camptothecin, or the derivative thereof is bound to the at least one cleavable linker.

According to a specific embodiment of the present invention, the prodrug as defined above comprises (i) 2-pyrollinodoxorubicin, morpholinodoxorubicin, diacetatoxypentyldoxorubicin, doxorubicin, camptothecin, paclitaxel, or a derivative thereof, (ii) a receptor targeted group, selected from the group consisting of folic acid derivatives, (iii) at least one cleavable linker selected from the group consisting of acid-labile linkers, and (iv) a maleinimide or a derivative thereof as the protein-binding moiety, wherein 2-pyrollinodoxorubicin, morpholinodoxorubicin, diacetatoxypentyldoxorubicin, doxorubicin, paclitaxel, camptothecin, or a derivative thereof is bound to the at least one cleavable linker.

Another aspect of the present invention relates to a pharmaceutical composition, comprising the prodrug as defined above, and optionally a pharmaceutically acceptable carrier and/or a pharmaceutically acceptable adjuvent and/or a diluent.

The pharmaceutical composition may for example contain solvents and diluents such as sodium chloride solution or a solution containing any pharmaceutically acceptable buffer. Moreover, the pharmaceutical composition of the present invention may be in any form suitable for administration to a patient, for example in an injectable form, as a tablet or a capsule, or as a composition for inhalation.

According to a specific embodiment, the above-defined pharmaceutical composition is for treatment of a disease selected from the group consisting of cancer, autoimmune diseases, acute or chronic inflammatory diseases, and diseases caused by viruses and/or microorganisms.

Another aspect of the present invention relates to the use of the prodrug as defined above in the manufacturing of a pharmaceutical composition for treating or diagnosing a patient suffering from a disease selected from the group consisting of cancer, autoimmune diseases, acute or chronic inflammatory diseases, and diseases caused by viruses and/or microorganisms.

According to a further specific embodiment, the above-defined pharmaceutical composition is for the treatment of cancer in which one type of receptor or antigen is overexpressed compared to healthy tissue.

According to another embodiment of the present invention, the prodrug as defined above may be comprised in a kit, which may further contain one or more adjuvants, such as a buffer or a pharmaceutically acceptable carrier.

The figures show:

Figure 4:
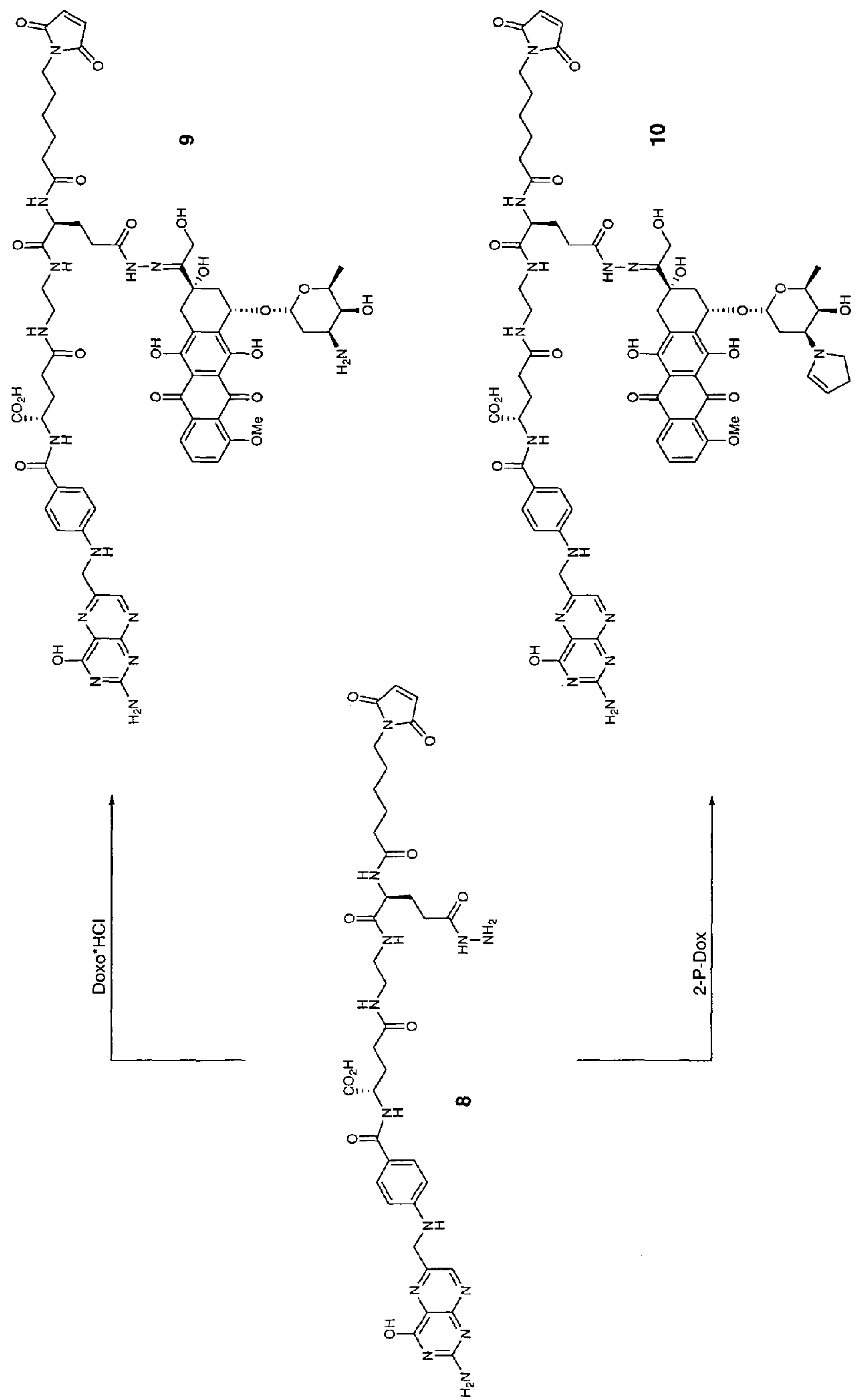

FIG. 4 shows the structure and the synthesis of the folic acid maleimide derivative 8 as a precursor for the synthesis of the prodrugs 8 and 9 according to the present invention, The present invention will be further illustrated in the following examples, without any limitation thereto.

EXAMPLES

Example 1

According to the present invention, a prodrug is prepared wherein the pharmaceutically active compound is doxorubicin, the receptor targeting moiety is a cyclic $[c(RGDF)]_2$-peptide and the protein-binding moiety is maleinimide. The pharmaceutically active compound, i.e. doxorubicin, is released from the prodrug through cleavage of a peptide linker cleaved by MMP-2 or MMP-9.

Figure 1:
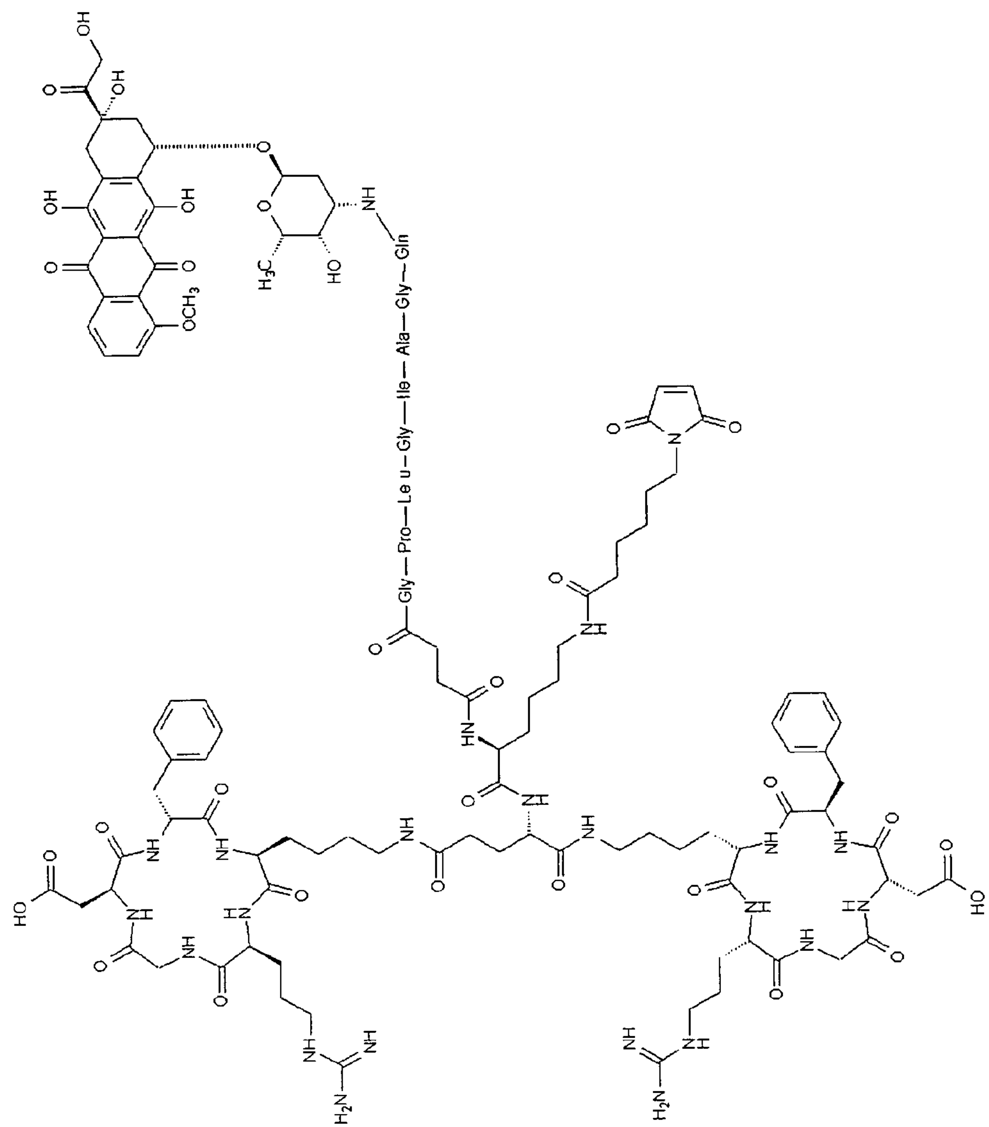
FIG. 1 shows the structure of a prodrug according to the present invention, wherein the pharmaceutically active compound is doxorubicin, the receptor targeting moiety is a cyclic $[c(RGDF)]_2$-peptide and the protein-binding moiety is maleinimide. The doxorubicin is released from a peptide linker cleaved by MMP-2 or MMP-9.

The prodrug according to the present invention is advantageously capable of binding in situ to a thiol-containing macromolecular carrier such as albumin, thus enabling a more specific transport to the target tissue in a patient due to passive targeting. Moreover, the combination of a pharmaceutically active compound bound to a cleavable linker with a receptor targeting moiety advantageously enables the treatment under surprisingly high specificity. In particular, by combining the receptor targeting moiety, e.g. a cyclic $[c(RGDF)]_2$-peptide that interacts with the integrin $\alpha v\beta 3$ over-expressed in tumor blood vessel, and a pharmaceutically active compound, i.e. doxorubicin, in a prodrug, it is surprisingly achieved to efficiently enrich the resulting conjugate in the target tissue through a combination of active and passive targeting with high selectivity and, after cleavage of the active agent through MMP-2 and/or MMP-9 which are both over-expressed in the tumor, to release the active agent in the tumor (cf. for example FIG. 1).

Example 2

Figure 2:
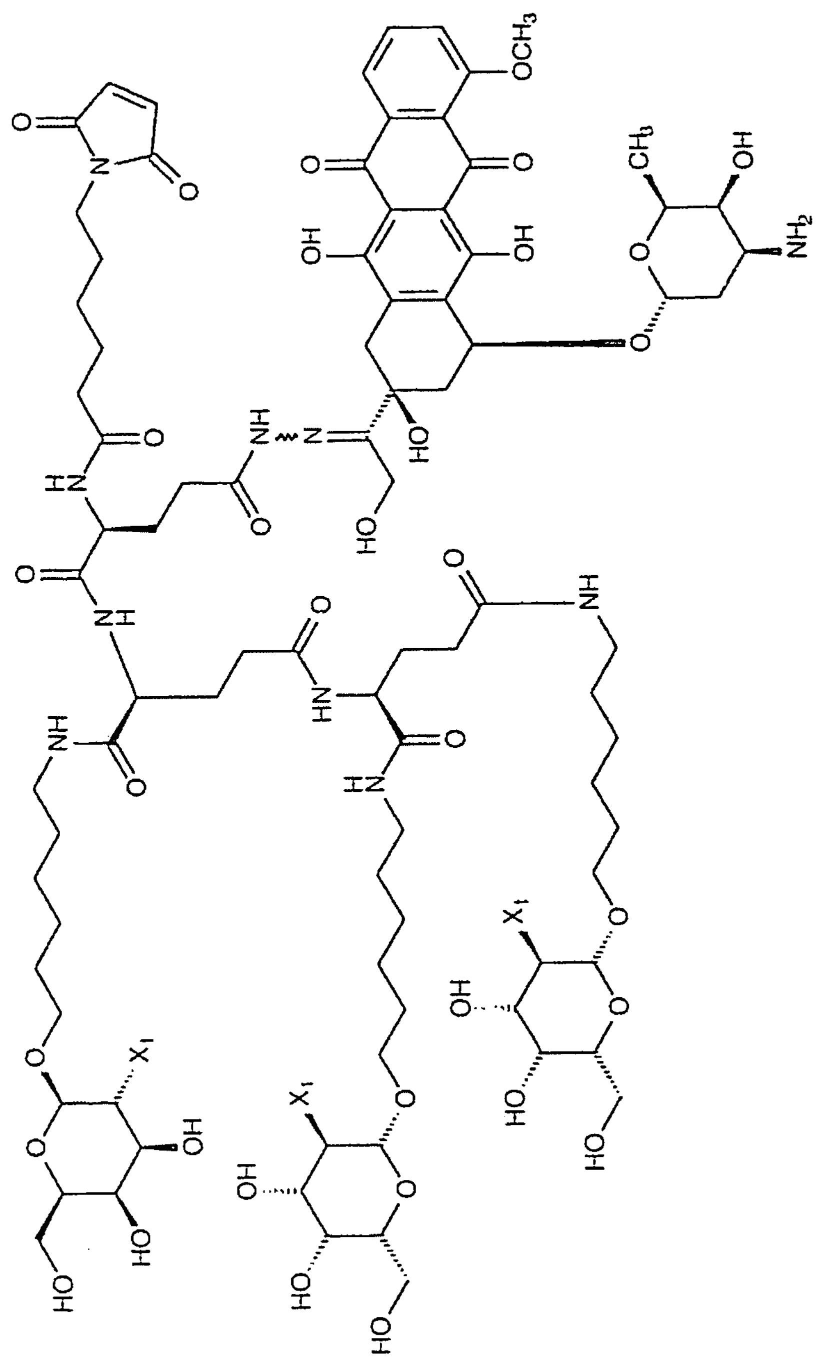
FIG. 2 shows the structure of a prodrug according to the present invention, wherein the pharmaceutically active compound is doxorubicin, the receptor targeting moiety is a Gal-cluster ($X_1$=OAc) or a GalNAc-cluster ($X_1$=NHAc) and the protein-binding moiety is maleinimide. The doxorubicin is released from an acid-labile linker.

According to the present invention, a prodrug is prepared wherein the pharmaceutically active compound is doxorubicin, the receptor targeting moiety is a Gal-cluster ($X_1$=OAc) or a GalNAc-cluster ($X_1$=NHAc) and the protein-binding moiety is maleinimide (cf. for example FIG. 2). The pharmaceutically active compound, i.e. doxorubicin, is released from the prodrug by cleavage of an acid-labile linker.

The prodrug according to the present invention is advantageously capable of binding in situ to a thiol-containing macromolecular carrier such as albumin, thus enabling a more specific transport to the target tissue in a patient due to passive targeting. Moreover, the combination of a pharmaceutically active compound bound to a cleavable linker with a receptor targeting moiety advantageously enables the treatment under surprisingly high specificity. In particular, by combining the receptor targeting moiety, e.g. a Gal-cluster ($X_1$=OAc) or a GalNAc-cluster ($X_1$=NHAc) that interacts with the asialoglycoprotein receptor on liver tumor cells, and a pharmaceutically active compound, e.g. doxorubicin, in a prodrug, it is surprisingly achieved to efficiently enrich the resulting conjugate in the target tissue through a combination of active and passive targeting with high selectivity and, after acid-cleavage of the active agent to release the active agent in the tumor.

Example 3

Figure 3:
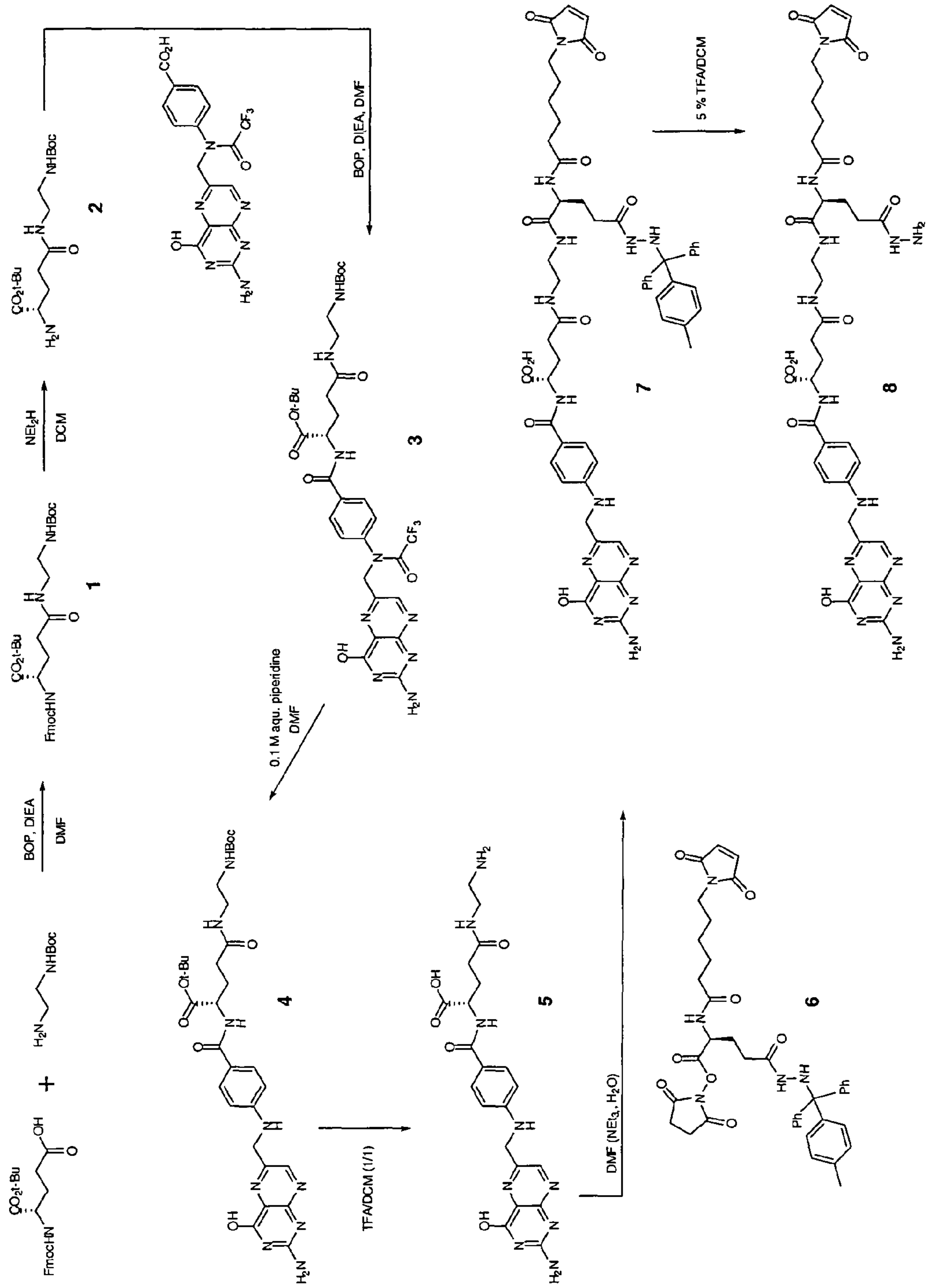
FIG. 3 shows the structure of prodrugs 9 and 10 according to the present invention, wherein the pharmaceutically active compound is doxorubicin or 2-pyrollinodoxorubicin, the receptor targeting moiety is folic acid and the protein-binding moiety is maleinimide. 2-Pyrollinodoxorubicin or doxorubicin is released from an acid-labile linker.

According to the present invention, prodrugs 9 and 10 are prepared wherein the pharmaceutically active compound is doxorubicin or 2-pyrollinodoxorubicin (2-PDox), the receptor targeting moiety is folic acid and the protein-binding moiety is maleinimide (cf. for example FIGS. 3 and 4). The pharmaceutically active compound, i.e. doxorubicin or 2-pyrollinodoxorubicin, is released from the prodrug by cleavage of an acid-labile linker. The prodrug according to the present invention is advantageously capable of binding in situ to a thiol-containing macromolecular carrier such as albumin, thus enabling a more specific transport to the target tissue in a patient due to passive targeting as well as due to active targeting through binding and uptake by the folate receptor that is over-expressed by tumor cells.

The prodrugs 9 and 10 were synthesized according to FIG. 3, the linker 8 was prepared according to FIG. 4 as described below.

Preparation of 2: A solution of benzotriazole-1-yl-oxy-tris-(dimethylamino)-phosphonium hexafluorophosphate (BOP, 13.3 g, 0.030 mmol, 1.2 equiv.) in dry DMF (5 mL) and diisopropylethylamine (DIEA, 4.1 mL, 0.024 mmol, 1 equiv.) was added to a solution of N-α-Fmoc-L-glutamic acid α-tert-butyl ester (10.24 g, 0.024 mmol, 1 equiv.) and N-(tert-butoxycarbonyl)-ethanolamine (3.85 g, 0.024 mmol, 1 equiv.) in dry DMF (30 mL). The solution was stirred at room temperature over night and precipitated with $H_2O$ (800 mL). The white precipitate was washed with $H_2O$ (2×30 mL) and dried in vacuo. The material was used without further purification. Diethylamine (460 mL) was added to a solution of 1 in DCM (320 mL) and the mixture was stirred at room temperature for 2 hours. The solvent was removed in vacuo. The residue was purified by column chromatography on silica gel with ethyl acetate/MeOH (4/1, v/v) to obtain a brown resin (6.2 g).

Preparation of 3: A solution of BOP (65 mg, 0.147 mmol, 1.2 equiv.) and DIEA (25 μL, 0.147 mmol, 1.2 equiv.) in dry DMF (1 mL) was added to a solution of 2 (51 mg, 0.147 mmol, 1.2 equiv.), $N^{10}$-(trifluoroacetyl)pteroic acid (50 mg, 0.122 mmol, 1 equiv.) and DIEA (21 μL, 0.122 mmol, 1 equiv.) in dry DMF (1 mL). The clear yellow solution was stirred at room temperature for 2 hours and precipitated with $Et_2O$ (80 mL). The precipitate was washed with $Et_2O$ (2×10 mL), dried in vacuo and purified by column chromatography on silica gel with a linear gradient of $CHCl_3$/MeOH (10/1, v/v) to $CHCl_3$/MeOH (1/1, v/v) to obtain a yellow substance (62 mg).

Preparation of 4: Compound 3 (600 mg, 0.816 mmol,) and 0.1 M aqueous piperidine (9 mL) in dry DMF (4 mL) was stirred at room temperature for 30 min. After addition of THF (40 mL) the solution was precipitated with $Et_2O$ (400 mL).

The yellow precipitate was washed with $Et_2O$ (2×10 mL) and dried in vacuo to obtain a yellow product (300 mg).

Preparation of 5: A solution of 4 (288 mg, 0.391 mmol,) in DCM/TFA (7 mL, 1/1, v/v) was stirred for 5 hours. The solution was precipitated with $Et_2O$ (120 mL). The yellow precipitate was washed with $Et_2O$ (2×20 mL) and dried in vacuo to obtain a yellow product (240 mg).

Preparation of 6: DMAP (0.1 equiv, 14.8 mmol, 1.81 g) and DIPC (1.5 equiv., 222.3 mmol, 34.5 mL) were added under nitrogen atmosphere slowly at 0° C. to a solution of Cbz-Glu-OtBu (1 equiv., 148.2 mmol, 50 g) and tetrt.butyl-carbazate (1.5 equiv., 222.3 mmol, 29.4 g) in dry DCM (100 mL). The mixture was stirred then at RT for 16 h. The solid was removed by suction filtration and washed with DCM. The organic layer was extracted with 0.1 M HCl (10×100 mL). The organic phase was then extracted with brine, water, dried and the solvent was removed under reduced pressure to give Cbz-Glu-NH—NH-BOC as a white solid (66.6 g) 60 g Cbz-Glu-NH—NH-BOC was dissolved under nitrogen in dry methanol (200 mL). Pd/C (10%, 2.5 g) was added and a hydrogen balloon was applied to the flask. The reaction mixture was stirred au RT for 4 d during which the balloons were exchanged with new ones. The suspension was then diluted with methanol, filtered over celite and the solvent was removed under reduced pressure. The oily rest was purified by FC on silica eluting with $CHCl_3$/MeOH 20:1 to give H-Glu-NH—NH-BOC as a white solid (42 g). The 6-maleimidocaproic acid chloride was prepared from maleimidocaproic acid (82.78 mmol, 17.35 g) and oxalic acid chloride (1.0 equiv, 82.78 mmol, 9.93 mL) in dry DCM (180 mL). Then dry trietylamine (82.8 mmol, 11.47 mL) was added at RT under nitrogen atmosphere to a solution of H-Glu-NH—NH-BOC (82.8 mmol, 26.36 g) in dry DCM (300 mL) followed by slowly adding the solution of the 6-maleimidocaproic acid chloride. The reaction solution was stirred at RT for 18 h. The solvent was removed under reduced pressure. The oily residue was purified by flash chromatography on silica eluting with EE/hexane (i) 1:1, (i) 2:1, (i) 4:1 to give EMC-Glu-NH—NH-BOC as a white solid (36 g, 76%).

A solution of EMC-Glu-NH—NH-BOC (32.4 g) and TFA (165 mL) in DCM (165 mL) was stirred at RT for 80 min after which diethyl ether (4 L) was added. The precipitated product was collected by suction filtration, washed with ether and dried yielding EMC-Glu-NH—$NH_2$ TFA (20 g).

A stirred suspension of EMC-Glu-NH—$NH_2$ TFA (11 mmol, 5 g,) in dry DCM (50 mL) under nitrogen atmosphere at RT was treated with trimethylsilyl chloride (2.1 equiv., 23.1 mmol, 3 mL) and DIEA (1.05 equiv., 11.55 mmol, 1.9 mL). The mixture was heated at reflux for 1 h, and then cooled to 0° C. DIEA (3.1 equiv, 63.8 mmol, 5.8 mL) was added, followed by methyltritylchloride (1.05 equiv, 11.55 mmol, 3.41 g). The reaction was stirred at room temperature for 16 h. Methanol (50 mL) was added and the solution was stirred for 5 min. The solvent was evaporated at 30° C., and the residue was partitioned between DCM and pH 5 buffer (acetate). The organic phase was washed with more pH 5 buffer, water, and brine, dried and the solvent was evaporated. The oily residue was purified by FC on silica eluting with $CHCl_3/CH_3OH$ (10:1) to give EMC-Glu-NH—NH-Mtt as a pale yellow foam (4.5 g).

A stirred solution of EMC-Glu-NH—NH-Mtt (6.22 mmol, 3.8 g) and N-hydroxy succinimide (1.05 equiv, 6.60 mmol, 755 mg) in dry THF (25 mL) at 0° C. was treated with N,N'-dicyclodicarbodiimide (1.05 equiv, 6.60 mmol, 1.36 g). After 20 min, the mixture was allowed to warm to RT and was stirred for 16 h. The solid by-product was filtered off, washed with dry THF, and the solvent was evaporated and then purified by flash chromatography on diol eluting with THF/hexane (1:1) to furnish 6 as a white solid (2.70 g).

Preparation of 8: Compound 5 (200 mg, 0.37 mmol, 1 equiv.) and the maleimide derivative 6 (262 mg, 0.37 mmol, 1 equiv) in dry DMF (8 mL) were stirred for 5 hours. DMF was removed in vacuo and the resulting solid dissolved in 6 mL DCM/2 TFA and stirred for 1 h and the solution then precipitated with $Et_2O$ (50 mL). The yellow precipitate was washed with $Et_2O$ (2×10 mL) and dried in vacuo to obtain a yellow product (155 mg).

Preparation of 9 and 10: Compound 8 (60 mg, 0.064 mmol) were reacted with 12.2 mg doxorubicin HCl (0.021 mmol) or 12.8 2-pyrollinodoxorubicin (0.021 mmol) in 30-40 mL dry methanol for 3 days in the dark. The solution was concentrated in vacuo to approximately 10 mL and 9 and 10 were isolated by crystallization with dry isopropanol/$Et_2O$ (2:1) and washed twice with 10 mL dry $Et_2O$ and the red compounds dried in vacuo. 9: 7.4 mg, 10: 8.3 mg.

The invention claimed is:

1. A prodrug, comprising (i) at least one pharmaceutically and/or diagnostically active compound, (ii) at least one receptor and/or antigen targeting moiety, wherein the receptor and/or antigen targeting moiety is a peptide derivative comprising the sequence (Pyr)-His-Trp-Ser-Tyr-Lys-Leu-Arg-Pro-Gly-NH2 (SEQ ID NO: 1), (iii) at least one cleavable linker, and (iv) a protein-binding moiety which binds in situ to serum proteins following administration of the prodrug, wherein the at least one pharmaceutically and/or diagnostically active compound is bound to the at least one cleavable linker, wherein the at least one cleavable linker, the protein binding moiety, and the at least one receptor and/or antigen targeting moiety are joined to form a branched structure; and wherein the protein-binding moiety is selected from the group consisting of a maleinimide group, a halogenacetamide group, a halogenacetate group, a pyridylthio group, a vinylcarbonyl group, an aziridin group, a disulfide group, a substituted or unsubstituted acetylene group, and a hydroxysuccinimide ester group.

2. The prodrug according to claim 1, wherein the at least one pharmaceutically and/or diagnostically active compound is selected from the group consisting of a cytostatic agent, a cytokine, an immunosuppressant, an antirheumatic, an antiphlogistic, an antibiotic, an analgesic, a virostatic, and an antimycotic agent, a transcription factor inhibitor, a cell cycle modulator, a MDR modulator, a proteasome or protease inhibitor, an apoptosis modulator, an enzyme inhibitor, an angiogenesis inhibitor, a hormone or hormone derivative, a radioactive substance, a light emitting substance, and a light absorbing substance.

3. The prodrug according to claim 1, wherein the at least one pharmaceutically and/or diagnostically active compound is a cytostatic agent selected from the group consisting of N-nitrosoureas, the anthracyclines doxorubicin, 2-pyrollinoanthracycline, morpholinoanthracycline, diacetatoxyalkylanthracycline, daunorubicin, epirubicin, idarubicin, mitoxantrone and ametantrone, and any derivatives thereof; the alkylating agents chlorambucil, bendamustine, melphalan, and oxazaphosphorines, and any derivatives thereof; the antimetabolites 5-fluorouracil, 2'-deoxy-5-fluorouridine, cytarabine, cladribine, fludarabine, pentostatine, gemcitabine and thioguanine, and any derivatives thereof; the folic acid antagonists methotrexate, raltitrexed, pemetrexed and plevitrexed, the taxanes paclitaxel and docetaxel, and any derivatives thereof; the camptothecins topotecan, irinotecan, 9-aminocamptothecin and camptothecin, and any derivatives thereof; the Vinca alkaloids vinblastine, vincristine, vindesine and vinorelbine, and any derivatives thereof; calicheamicins and any derivatives thereof; maytansinoids and any derivatives thereof; auristatins and any derivatives thereof; epothilones and any derivatives thereof; bleomycin, dactinomycin, plicamycin, mitomycin C and cis-configured platinum(II) complexes.

4. The prodrug according to claim 1, wherein the cleavable linker can be cleaved hydrolytically and/or enzymatically and/or pH-dependently.

5. The prodrug according claim 1, wherein the protein-binding moiety binds in situ to cysteine-34 of albumin.

6. The prodrug according to claim 1, wherein the pharmaceutically and/or diagnostically active compound contains one or more radionuclides, one or more positron emitters, one or more NMR contrast agents, one or more fluorescent compound(s), or one or more near-infrared contrast agents.

7. The prodrug according to claim 1, wherein (i) the at least one pharmaceutically and/or diagnostically active compound is selected from the group consisting of doxorubicin, 2-pyrollinodoxorubicin, morpholinodoxorubicin, diacetatoxypentyldoxorubicin, paclitaxel, camptothecin, or a derivative thereof;

(ii) the at least one cleavable linker is selected from the group consisting of an acid-labile linker and a linker cleavable by MMP2 and/or MMP9; and (iii) the protein-binding moiety is maleinimide or a derivative thereof, and wherein the doxorubicin, 2-pyrollinodoxorubicin, morpholinodoxorubicin, diacetatoxypentyl-doxorubicin, paclitaxel or camptothecin, or the derivative thereof is bound to the at least one cleavable linker.

8. A pharmaceutical composition, comprising the prodrug according to claim 1, and optionally a pharmaceutically acceptable carrier and/or a pharmaceutically acceptable adjuvent and/or a diluent.

9. A pharmaceutical composition, comprising the prodrug according to claim 8, for the treatment of a disease selected from cancer, autoimmune diseases, acute or chronic inflammatory diseases, and diseases caused by viruses and/or microorganisms.

* * * * *

SEQUENCE LISTING

```
<160> NUMBER OF SEQ ID NOS: 46

<210> SEQ ID NO 1
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Pyr

<400> SEQUENCE: 1

Xaa His Trp Ser Tyr Lys Leu Arg Pro Gly
1               5                   10


<210> SEQ ID NO 2
<211> LENGTH: 4
<212> TYPE: PRT
<213> ORGANISM: Artificial Sequence
<220> FEATURE:
<223> OTHER INFORMATION: Synthetic
```

<400> SEQUENCE: 2

Ala Leu Ala Leu
1

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Ser Ser Tyr Tyr Ser Arg
1 5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Phe Pro Lys Phe Phe Ser Arg Gln
1 5

<210> SEQ ID NO 5
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: X is Nph

<400> SEQUENCE: 5

Lys Pro Ile Glu Phe Xaa Arg Leu
1 5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Gly Pro Leu Gly Ile Ala Gly Gln
1 5

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Gly Pro Gln Gly Ile Trp Gly Gln
1 5

<210> SEQ ID NO 8
<211> LENGTH: 4
<212> TYPE: PRT

```
<213> ORGANISM: Artificial Sequence
<220> FEATURE:
<223> OTHER INFORMATION: Synthetic

<400> SEQUENCE: 8

Gly Phe Leu Gly
1


<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Ser Pro Leu Trp Arg Asn Ser Val Leu
1               5


<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Thr Ser Pro Leu Asn Ile His Asn Gly Gln Lys Leu
1               5                   10


<210> SEQ ID NO 11
<211> LENGTH: 14
<212> TYPE: PRT
<213> ORGANISM: Artificial Sequence
<220> FEATURE:
<223> OTHER INFORMATION: Synthetic

<400> SEQUENCE: 11

Met Tyr Trp Gly Asp Ser His Trp Leu Gln Tyr Trp Tyr Glu
1               5                   10


<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Met Cys Pro Lys His Pro Leu Gly Cys
1               5


<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

His Leu Gln Ile Gln Pro Trp Tyr Pro Gln Ile Ser
1               5                   10


<210> SEQ ID NO 14
<211> LENGTH: 12
<212> TYPE: PRT
<213> ORGANISM: Artificial Sequence
```

<220> FEATURE:
<223> OTHER INFORMATION: Synthetic

<400> SEQUENCE: 14

His Glu Trp Ser Tyr Leu Ala Pro Tyr Pro Trp Phe
1 5 10

<210> SEQ ID NO 15
<211> LENGTH: 6
<212> TYPE: PRT
<213> ORGANISM: Artificial Sequence
<220> FEATURE:
<223> OTHER INFORMATION: Synthetic

<400> SEQUENCE: 15

Lys Cys Cys Tyr Ser Leu
1 5

<210> SEQ ID NO 16
<211> LENGTH: 17
<212> TYPE: PRT
<213> ORGANISM: Artificial Sequence
<220> FEATURE:
<223> OTHER INFORMATION: Synthetic

<400> SEQUENCE: 16

Cys Glu Ser Leu Trp Gly Gly Leu Met Trp Thr Ile Gly Leu Ser Asp
1 5 10 15

Cys

<210> SEQ ID NO 17
<211> LENGTH: 17
<212> TYPE: PRT
<213> ORGANISM: Artificial Sequence
<220> FEATURE:
<223> OTHER INFORMATION: Synthetic

<400> SEQUENCE: 17

Cys Asn Ile Trp Gly Val Val Leu Ser Trp Ile Gly Val Phe Pro Glu
1 5 10 15

Cys

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Leu Thr Val Gly Pro Trp Gly
1 5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Cys Asp Arg Gly Asp Cys Phe Cys
1 5

<210> SEQ ID NO 20

```
<211> LENGTH: 11
<212> TYPE: PRT
<213> ORGANISM: Artificial Sequence
<220> FEATURE:
<223> OTHER INFORMATION: Synthetic

<400> SEQUENCE: 20

Ala Cys Asp Cys Arg Gly Asp Cys Phe Cys Gly
1               5                   10


<210> SEQ ID NO 21
<211> LENGTH: 13
<212> TYPE: PRT
<213> ORGANISM: Artificial Sequence
<220> FEATURE:
<223> OTHER INFORMATION: Synthetic

<400> SEQUENCE: 21

Cys Asn Gly Arg Cys Val Ser Gly Cys Ala Gly Arg Cys
1               5                   10


<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Cys Val Cys Asn Gly Arg Met Glu Cys
1               5


<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Asn Gly Arg Ala His Ala
1               5


<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

Cys Gly Ser Leu Val Arg Cys
1               5


<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

Cys Gly Leu Ser Asp Ser Cys
1               5


<210> SEQ ID NO 26
<211> LENGTH: 10
```

<212> TYPE: PRT
<213> ORGANISM: Artificial Sequence
<220> FEATURE:
<223> OTHER INFORMATION: Synthetic

<400> SEQUENCE: 26

Thr Ala Ala Ser Gly Val Arg Ser Met His
1 5 10

<210> SEQ ID NO 27
<211> LENGTH: 10
<212> TYPE: PRT
<213> ORGANISM: Artificial Sequence
<220> FEATURE:
<223> OTHER INFORMATION: Synthetic

<400> SEQUENCE: 27

Leu Thr Leu Arg Trp Val Gly Leu Met Ser
1 5 10

<210> SEQ ID NO 28
<211> LENGTH: 10
<212> TYPE: PRT
<213> ORGANISM: Artificial Sequence
<220> FEATURE:
<223> OTHER INFORMATION: Synthetic

<400> SEQUENCE: 28

Cys Thr Thr His Trp Gly Phe Thr Leu Cys
1 5 10

<210> SEQ ID NO 29
<211> LENGTH: 15
<212> TYPE: PRT
<213> ORGANISM: Artificial Sequence
<220> FEATURE:
<223> OTHER INFORMATION: Synthetic

<400> SEQUENCE: 29

Asn Arg Ser Leu Lys Arg Ile Ser Asn Lys Arg Ile Arg Arg Lys
1 5 10 15

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

Arg Arg Lys Arg Arg Arg
1 5

<210> SEQ ID NO 31
<211> LENGTH: 7
<212> TYPE: PRT
<213> ORGANISM: Artificial Sequence
<220> FEATURE:
<223> OTHER INFORMATION: Synthetic

<400> SEQUENCE: 31

Ala Thr Trp Leu Pro Pro Arg
1 5

<210> SEQ ID NO 32
<211> LENGTH: 9
<212> TYPE: PRT

<213> ORGANISM: Artificial Sequence
<220> FEATURE:
<223> OTHER INFORMATION: Synthetic

<400> SEQUENCE: 32

Cys Pro Gly Pro Glu Gly Ala Gly Cys
1 5

<210> SEQ ID NO 33
<211> LENGTH: 7
<212> TYPE: PRT
<213> ORGANISM: Artificial Sequence
<220> FEATURE:
<223> OTHER INFORMATION: Synthetic

<400> SEQUENCE: 33

Ser Met Ser Ile Ala Arg Leu
1 5

<210> SEQ ID NO 34
<211> LENGTH: 7
<212> TYPE: PRT
<213> ORGANISM: Artificial Sequence
<220> FEATURE:
<223> OTHER INFORMATION: Synthetic

<400> SEQUENCE: 34

Val Ser Phe Leu Glu Tyr Arg
1 5

<210> SEQ ID NO 35
<211> LENGTH: 15
<212> TYPE: PRT
<213> ORGANISM: Artificial Sequence
<220> FEATURE:
<223> OTHER INFORMATION: Synthetic

<400> SEQUENCE: 35

Pro Arg Pro Gly Ala Pro Leu Ala Gly Ser Trp Pro Gly Thr Ser
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: Synthetic

<400> SEQUENCE: 36

Asp Arg Trp Arg Pro Ala Leu Pro Val Val Leu Phe Pro Leu His
1 5 10 15

<210> SEQ ID NO 37
<211> LENGTH: 15
<212> TYPE: PRT
<213> ORGANISM: Artificial Sequence
<220> FEATURE:
<223> OTHER INFORMATION: Synthetic

<400> SEQUENCE: 37

Ala Ser Ser Ser Tyr Pro Leu Ile His Trp Arg Pro Trp Ala Arg
1 5 10 15

<210> SEQ ID NO 38
<211> LENGTH: 12
<212> TYPE: PRT
<213> ORGANISM: Artificial Sequence

```
<220> FEATURE:
<223> OTHER INFORMATION: Synthetic

<400> SEQUENCE: 38

His Thr Met Tyr Tyr His His Tyr Gln His His Leu
1               5                   10


<210> SEQ ID NO 39
<211> LENGTH: 9
<212> TYPE: PRT
<213> ORGANISM: Artificial Sequence
<220> FEATURE:
<223> OTHER INFORMATION: Synthetic

<400> SEQUENCE: 39

Cys Gly Asn Lys Arg Thr Arg Gly Cys
1               5


<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Cys Gly Asn Arg Thr Arg Gly Cys
1               5


<210> SEQ ID NO 41
<211> LENGTH: 15
<212> TYPE: PRT
<213> ORGANISM: Artificial Sequence
<220> FEATURE:
<223> OTHER INFORMATION: Synthetic

<400> SEQUENCE: 41

Asn Gly Glu Ile Glu Trp Tyr Ser Trp Val Thr His Gly Met Tyr
1               5                   10                  15


<210> SEQ ID NO 42
<211> LENGTH: 9
<212> TYPE: PRT
<213> ORGANISM: Artificial Sequence
<220> FEATURE:
<223> OTHER INFORMATION: Synthetic

<400> SEQUENCE: 42

Cys Cys Asp Arg Gly Asp Cys Phe Cys
1               5


<210> SEQ ID NO 43
<211> LENGTH: 6
<212> TYPE: PRT
<213> ORGANISM: Artificial Sequence
<220> FEATURE:
<223> OTHER INFORMATION: Synthetic

<400> SEQUENCE: 43

Cys Cys Asn Gly Arg Cys
1               5


<210> SEQ ID NO 44
<211> LENGTH: 9
<212> TYPE: PRT
<213> ORGANISM: Artificial Sequence
<220> FEATURE:
```

```
<223> OTHER INFORMATION: Synthetic

<400> SEQUENCE: 44

Cys Gly Asn Lys Arg Thr Arg Gly Cys
1               5


<210> SEQ ID NO 45
<211> LENGTH: 13
<212> TYPE: PRT
<213> ORGANISM: Artificial Sequence
<220> FEATURE:
<223> OTHER INFORMATION: Synthetic

<400> SEQUENCE: 45

Cys Gly Phe Glu Cys Val Arg Gln Cys Pro Glu Arg Cys
1               5                   10


<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Arg Gly Asp Phe Arg Gly Asp Phe
1               5
```